United States Patent [19]

Alliger et al.

[11] Patent Number: 5,582,829
[45] Date of Patent: Dec. 10, 1996

[54] SONICATED BORRELIA BURGDORFERI VACCINE

[75] Inventors: Howard M. Alliger, Melville, N.Y.; Alan Frey, Highland Park, N.J.

[73] Assignee: Rx Technologies, Inc., Garden City, N.Y.

[21] Appl. No.: 921,303

[22] Filed: Jul. 28, 1992

Related U.S. Application Data

[63] Continuation-in-part of Ser. No. 505,193, Apr. 5, 1990, abandoned.

[51] Int. Cl.⁶ .............................. A61K 39/02; C12N 13/00
[52] U.S. Cl. ..................................... 424/234.1; 435/173.7; 435/173.9
[58] Field of Search .......................... 424/88, 92, 234.1; 435/173, 173.7, 173.9

[56] References Cited

U.S. PATENT DOCUMENTS

| | | | |
|---|---|---|---|
| 3,642,574 | 2/1972 | Okazaki et al. | 424/229.1 |
| 3,676,547 | 7/1972 | Galloway et al. | 424/265.1 |
| 3,993,743 | 11/1976 | Hanson | 435/7.22 |
| 4,066,744 | 1/1978 | Price et al. | 435/7.36 |
| 4,182,753 | 1/1980 | Saltarelli | 424/115 |
| 4,298,597 | 11/1981 | Acres et al. | 424/241.1 |
| 4,721,617 | 1/1988 | Johnson | 424/234.1 |
| 4,797,285 | 1/1989 | Barenholz et al. | 424/450 |
| 4,837,028 | 6/1989 | Allen | 424/1.21 |
| 5,178,859 | 1/1993 | Simon et al. | 424/139.1 |

OTHER PUBLICATIONS

"Borrelia Burgdorferi strain 25015: Characterization". . . by Errol FiKrig, et al., Apr. 1, 1992, The Journal of Immunology, pp. 2256–2260.

"Lyme Borreliosis in Selected Strains and". . . by Stephen Barthold, et al., Jan. 8, 1990, The Journal of Infectious Diseases, vol. 162, pp. 133–138.

Alliger H., American Laboratory Oct. 1975.

Fikrig et al, Science 250: 553–556, 1990.

Boslego et al, "Gonorrhea Vaccines" in Vaccines and Immunotherapy, S. J. Cryz, Jr. ed, Pergamon Press, pp. 211–223, 1991.

Kallings et al, Lancet (I): 955–960, 1988.

Barbour et al, Journal of Infectious Diseases 152(3): 478–484, 1985.

Philipp et al. Infect. Immunity 61(7): 3047–3059, 1993.

Frikrig et al. Infect. Immunity 60(3): 773–777, 1992.

Preac–Mursic et al. Infection 20(6): 342–349, 1992

Edelman R. Vaccine 9: 531–532, 1991.

Frikrig et al. Infect. Immunity 61(6): 2553–2557, 1993.

*Primary Examiner*—James C. Housel
*Assistant Examiner*—Julie Krsek-Staples
*Attorney, Agent, or Firm*—Henry D. Coleman; R. Neil Sudol

[57] ABSTRACT

A process for the preparation of a vaccine from substantially viable spirochetal bacteria of Borrelia, preferably *Borrelia burgdorferi* having immunogenic or therapeutic properties and capable of inducing an immune or therapeutic response against Lyme Disease when administered to a patient is described. The product for use against Lyme Disease is produced by ultrasound treatment of substantially viable spirochetal bacteria of *Borrelia burgdorferi*. The invention produces a product and a method of treatment that can be used for the immunization and/or therapy of a patient against Lyme Disease to minimize or prevent the contraction of the disease or to treat the disease.

16 Claims, 7 Drawing Sheets

SONICATED BORRELIA BURGDORFERI VACCINE

This work has been supported by DARPA Grant No. N0014-90-J-2032. The United States Government retains certain rights in the invention.

This application is a continuation-in-part application of U.S. patent application Ser. No. 07/505,193, filed Apr. 5, 1990, abandoned, entitled "Production of Vaccine from Viruses or Cells, Product Produced Thereby and Method of Use."

This invention relates to a process for producing a vaccine from viruses or cells, the vaccine so produced, and the method of use of the vaccine. More particularly, this invention relates to a vaccine against *Borrelia burgdorferi*, the causative agent of Lyme disease in humans.

More particularly, this invention relates to a method wherein viruses or cells, and in particular, the spirochete *Borrelia burgdorferi* in substantially viable form, are disrupted using ultrasound. The resulting preparation can be used as a vaccine (for prevention and/or therapy) for the disease caused by the specific microorganism.

BACKGROUND OF THE INVENTION

Research has been focused for many years on the use of immunotherapy to prevent disease.

The major health problems still to be encountered in non-industrialized environments are those arising from infectious disease. Currently, all types of causative agents, including virus, bacteria and parasites are active sources of infection. The genetic variability of both viruses and parasites and the development of drug resistance in bacteria and parasites has underscored the need for broadly based vaccine development.

Success has been achieved for diseases such as smallpox, measles, tetanus and poliomyelitis but not for Herpes, Hepatitis, AIDS and a number of other major health problems. Approaches that have been successful (e.g., smallpox, polio) have employed attenuated strains of intact organisms that function both as immunogen and adjuvant. Recent strategies focused on defined peptide sequences alone have usually failed to elicit protective responses in vivo suggesting that the presentation of a combination of key antigens to the immune system of the host is the critical element in the overall process. Additional difficulties that have been experienced in the prior art include isolating antigens without modifying them in such a way that they lose the capability to raise protective antibodies or to sensitize cells of the immune system.

The prior art has generally taken two routes to elevate the immune response. One route has been to use immunoadjuvants which, in a non-specific manner, increase the immune responsiveness of the host, while the second route has been the eliciting of an antibody response using only the antigens.

Attempts to produce a protective immune response by the use of potential antigens isolated from viruses or cells have generally been unsuccessful. One problem is that the products solubilized from the viruses or cells often were found not to be immunogenic. Various theories have been proposed for the failure of the putative antigenic materials to produce a response. One possibility is that the physical or chemical methods employed to release or purify the antigens may be inadequate or resulted in denaturing the antigens. Another possibility is that the problem of producing a suitable solubilized or synthetic vaccine was that antigens either failed to reach the lymphocytes or did so insufficiently to activate them.

The present invention also relates to the production of a vaccine for use against Lyme Disease and the vaccine so produced.

Pathogenic bacteria continue to be a major source of disease in humans and animals. Improvements in minimizing bacterial contamination have made substantial inroads in eradicating or containing the spread of bacterial disease. Many bacterial infections can be effectively treated in the acute phase of infection with antibiotics. There are, however, a large number of diseases that escape early detection and don't respond to antibiotic treatment. Added to this is the possibility of misdiagnosis, inavailability of medical care, development of antibiotic resistant organisms or asymptmatic primary infection. Many bacterial and parasitic diseases are endemic to certain regions of the world; in particular, the tropics and sub-tropics. The problem is exacerbated in those areas suffering from inadequate water and sewage treatment.

An effective and convenient model for pathogenic bacteria is Lyme Disease caused by the spirochete *Borrelia burgdorferi. Borrelia burgdorferi* is closely related to several other tick-borne Borrelia which are causative agents for the very serious and debilitating disease, such as Relapsing Fever. Relapsing Fever, although rare in the United States, is endemic in Central America and Africa. Lyme Disease is quite common in the United States; in fact, it is the fastest growing vector-borne disease.

Infection of humans with the spirochete *Borrelia burgdorferi* generally results in the clinical disease more commonly known as Lyme Disease so named after the city in Connecticut where the geographic clustering of juvenile rheumatoid arthritis was first noted. The disease is transmitted by ticks and other major animal hosts are rodents, especially mice, and deer.

Infection by *Borrelia burgdorferi* provides a clinical model for the study of the molecular mechanisms underlying other potentially debilitating human disease. *Borrelia burgdorferi* closely resembles other Borrelia species which are human pathogens, such as *Borrelia hermsi*, and may be used as a model for creating vaccines against general Borrelia spirochetes. Moreover, *Borrelia burgdorferia* has been established in rodents isolated from infected ticks and humans, thus establishing an accurate laboratory model of Lyme Disease to be translated to the human system.

*Borrelia burgdorferi* is a gram-negative spirochete possessing a linear chromosome about 1,000 kb in size and also several extrachromosomal plasmids of varying size (approximately 8–60 kb). *Borrelia burgdorferi* possesses many kinds of proteins.

The clinical manifestation of the disease follows a multiphasic time course with different symptoms being demonstrated at each disease stage. Infection is initiated by passage through infected ticks. About 70% of human patients demonstrate a characteristic skin rash termed erythema chronica migrans (ECM) whose appearance is sometimes accompanied by fever or regional lymphadenopathy (The approximately 30% of infected patients who do not develop ECM proceed to late Stage 1 disease). Spirochetes, monocytes and neutrophils are present in the ECM lesion. Patient peripheral blood lymphocytes (PBL) are unresponsive to the organism in vitro and there is no circulating antispirochetal antibodies at this stage. Stage 2 infection is characterized by dissemination of the spirochete to many sites in the body including:

lymph, heart, neurologic, eyes, liver, respiratory, kidney and musculoskeletal systems. Headache of excruciating intensity is common although cerebrospinal fluid is normal. Patients are often incapacitated for several days with flu-like symptoms. At this stage, the PBL are responsible in vitro to *Borrelia burgdorferi* and serum antibodies are detectable beginning with an IgM response directed against the outer surface components of the spirochete. The temporal development of antibodies to specific antigens of *Borrelia burgdorferi* has been described in detail. With one notable exception, however, identification of protein antigens that are targets for the T cell immune response at any stage of the disease has not been completed.

The immune response in the early stage disease is characterized by infiltration of the ECM lesion by macrophage and neutrophils (PMN). PBL derived T cells are unresponsive to spirochetal antigens and serum does not contain circulating antibodies. Activity of Natural Killer (NK) cells in both the early and late stage Lyme Disease patients is inhibted but NK function is normal in patients that are in remission. Analysis in vitro has shown that NK cells are actually inhibited by spirochetes. There is a characteristic B-cell hyperactivity displayed by patients in various stages of Lyme Disease.

Late stage Lyme Disease is characterized by both circulating anti-spirochetal immunoglobulins and PBL T cell responsiveness to spirochetal antigens. The spirochetal antigens detected by the humoral immune response have been determined and most are cell surface antigens. With few exceptions, the epitopes recognized by the T cell immune response remain unknown.

Immune response in humans has been studied primarily involving the humoral immune response. Characteristic antibodies develop in most patients as a function of disease progression and it is this immune response that is used clinically to diagnose infection and efficacy of therapy. The cellular immune response is less well studied and understood.

One T cell epitope has been described by Shanafelt, et al., *J. Immunol.*, 146, 3985 (1991) and Yssel, et al., *J. Exp. Med.*, 174, 593 (1991). In these studies, T cells obtained from peripheral blood of Lyme Disease patients were expanded in vitro by co-culture to *Borrelia burgdorferi* using autologous B cells as antigen presenting cells. Spirochetal proteins were prepared by preparative SDS-PAGE and used to stimulate cloned anti-spirochetal T cells in vitro. Because of the apparent molecular weight of immunoreactive proteins, the DNA sequences of the *Borrelia burgdorferi* Hsp60 and OspA genes were deduced following molecular cloning. Lysates of *E. coli* expressing only the *Borrelia burgdorferi* Hsp 60 protein were used to stimulate the cloned anti-spirochetal T cells in vitro. Immunoreactivity to individual Hsp 60 peptides was determined using the proliferation assay. Using deletion mutants of the cloned Hsp60 gene specific peptide epitopes were determined to be targets for particular cloned anti-spirochetal T cells. However, the authors described several independent T cell clones and, since most did not react with the Hsp60 protein expressed in vitro, they conclude that there may be additional T cell epitopes contained in other proteins of *Borrelia burgdorferi*. The discovery of anti-OspA T cells substantiate that claim.

Since the spirochete apparently contains multiple antigens capable of eliciting an immune response, the question arises from the prior art research as to why the anti-spirochetal immune response fails to clear the organism from the body. No answer is presently clear. The present invention, however, attempts to address the limitation in the art by presenting multiple antigens of *Borrelia burgdorferi* in a sonicated cell mixture in such a way to produce prevention of Lyme disease in laboratory test animals which serve as useful and accurate models of the human system.

Because the spirochete is so unabundant that it avoids detection by direct methods in infected patients, the humoral immune response of patients is used diagnostically to detect infection. The disease course as revealed by specific changes in immune response may be important in disease progression.

The spirochete can be cultured in vitro only under stringent conditions which include reduced oxygen tension and a highly enriched nutrient medium. There are several isolates of the spirochete available and the various strains have been grouped on the basis of antibody recognition of specific surface antigens (serovar). Because of the considerable genetic similarities and means of transmission of the Borrelia species causing Lyme Disease and Relapsing Fever, the study of potential vaccine development for Lyme Disease was chosen as a model for spirochetal disease.

In the majority of cases Lyme Disease can be successfully treated with antibiotics, however, even with such treatment a number of cases with nevertheless proceed to chronic infection. At least 25% of the chronic disease does not elicit the characteristic ECM response which means that a substantial proportion of chronic disease cases are presented to the clinician as advanced stages of the disease. In addition, approximately, 1% of chronic disease patients either escape early stage detection or fail to respond to antibiotic therapy and consequently contract chronic Lyme Disease. Therefore, in a sizable number of instances, infection results in the development of debilitating late stage or chronic Lyme Disease.

OBJECTS OF THE PRESENT INVENTION

It is an object of the present invention to provide immunogenic dosage forms, including vaccines which produce enhanced immunogenic activity against a variety of diseases caused by viruses and certain cells.

It is an additional object of the present invention to provide immunogenic dosage forms, including vaccines, to immunize humans against Lyme Disease.

It is another object of the present to provide a therapeutic method for producing an immunogenic response in a patient to a virus or cell, especially including spirochetal bacteria such as Borrelia which are causative agents in the etiology of Lyme Disease and other diseases including Relapsing Fever, using the immunogenic dosage forms, including vaccines, according to the present invention.

It is still an additional object of the present invention to provide a method for producing immunogenic responses, especially including immunogenic responses against Borrelia, especially *Borrelia burgdorferi* using the immunogenic dosage forms of the present invention.

It is yet another object of the present invention to provide a method for producing an immunogenic reaction from an immunogenic organism even where the organism alone produces an ineffective (non-curative) immune response.

These and other objects of the present invention may be readily gleaned from the detailed description of the invention which is set forth herein.

SUMMARY OF THE INVENTION

The present invention relates to a suitable and effective antigenic mixture which is produced by the direct sonication of substantially viable viruses, bacteria or cells, especially in particular, spirochetal bacteria cells from the genus Borrelia, without the need for preliminary treatment and without the need for subsequent freezing and thawing or other substantial biochemical processing. The cell, bacteria or virus mass which is used in the vaccine is sonicated directly, i.e., without first being deactivated. This results in he disintegration of all of the viable cells, bacteria or viruses and exposes and releases antigen for an immunogenic response. The resulting mixture alone can be used as a vaccine without any further purification, separation or adjuvants. In certain preferred embodiments according to the present invention, the whole spirochetal bacteria sonicate mass may be centrifuged and the vesicle suspension used in immunogenic dosage form preferably in combination with an adjuvant.

The present invention also relates to an immunogenic dosage form as a vaccine, for inducing an immunogenic response to the spirochetal bacteria of the genus Borrelia, especially *Borrelia burgdorferi*. In this aspect of the present invention, spirochetes of the genus Borrelia, and in particular, *Borrelia burgdorferi*, are sonicated using the general methodologies described herein to produce whole spirochetal bacteria sonicates which may be used without any further purification as a vaccine against Lyme Disease or Relapsing Fever. In certain preferred embodiments according to this aspect of the present invention, the whole cell sonicate may be further purified by subjecting the sonicate to centrifugation to precipitate non-immunogenic, but not all, solids. The supernatant material may then be used as an immunogenic substance for purposes of using directly as or for preparing a vaccine against Lyme Disease. In preferred embodiments of the Lyme Disease vaccine aspect of this invention, the immunogenic material prepared from spirochetal bacteria of *Borrelia burgdorferi* is combined with an amount of an adjuvant effective to appreciably increase the immunogenicity of the sonicated material.

Known adjuvants which may be used in the present invention include Freund's Adjuvant (including complete Freund's Adjuvant), Ribi Adjuvant System (RAS available from Ribi ImmunoChem), TiterMax (a commercial alternative to RAS available from CytRx Corporation, Norcross, Ga., U.S.A.), aluminum salts (and other metal salts), Mycobacterial products (including muramyl dipeptides), Lipid A (in its monophosphoryl and diphosphoryl forms) and Bacillus of Calmett and Guerin (BCG), either the cell wall (CW) form or the residue (R) form and *Corynebacterium parvum* (in residue, cell wall or particulate (P) form).

As used herein, the term "adjuvant" will be understood to mean a substance or material administered together or in conjunction with the whole cell, bacteria or virus sonicates according to the present invention which increases the immune response over that of the whole cell, bacteria or virus sonicate. Adjuvants may be included in vaccine compositions according to the present invention in a number of forms including suspensions, solutions, emulsions (e.g., Freund's adjuvant), gels (aluminum hydroxide gel), or solid materials. The amount of adjuvant included in the dosage forms including vaccines according to the present invention is that amount effective for substantially increasing the immunogenic response of a patient relative to dosage forms which exclude adjuvants. In general, adjuvant may be included in an amount ranging from about 1/10 to about 10 times the amount of protein assayed in the cell, bacteria or virus sonicate. However, any effective amount of adjuvant may be used in the instant invention.

In certain aspects according to the present invention, a vaccine is prepared by sonicating whole cells, bacteria or viruses (and in particularly preferred embodiments, spirochetal bacteria of *Borrelia burgdorferi*) for a time and to a degree effective to render the otherwise infectious whole cells, bacteria or viruses completely inactive and without substantially changing the immunogenicity of antigens normally present at the surface of the whole cell, bacteria or virus. It is an unexpected result, especially in light of the prior art failure to produce an effective vaccine against Lyme Disease, that sonication of a whole spirochetal bacteria of *Borrelia burgdorferi* will produce an effective vaccine without further biochemical treatment.

The spirochete of *Borrelia burgdorferi* can be cultured in vitro under stringent conditions which include reduced oxygen tension and a highly enriched nutrient medium (for example, BSK media). The spirochete is generally stored frozen ($-80°$ C.) in 30% glycerol or other cryopreservation media. There are several isolates of the spirochete available and the various strains have been grouped on the basis of antibody recognition of specific surface antigens (serovar). The various isolates have been successfully passaged in rodents in the laboratory. Different strains of mice have been used to study the symptomotology of the disease since there appears to be variability in the physiological manifestation of symptoms in different strains of mice.

This invention also relates to a method of potentiating an immune response (i.e., humoral and/or cellular) in an animal, including a human, comprising the step of administering to such animal an immunizing dose of a composition produced according to the present invention, the composition preferably administered in the form of a vaccine and also preferably including an effective amount of adjuvant to enhance the immune response of the patient. Methods of potentiating an immune response utilizing the previously described immunogenic dosage forms, preferably including adjuvants, are also disclosed.

The fact that an active antigenic product results immediately from the sonicated microorganism is particularly surprising since the clear trend in immunology has been to provide greater and greater purification of antigenic components for the purpose of producing a vaccine. This invention takes the opposite approach, namely the use of the entire product which has been subjected to ultrasound, and in the case of a Lyme Disease vaccine, preferably to the further inclusion of an effective amount of an adjuvant to boost the inoculation with whole cell sonicate. Thus, the resulting product contains a full range of components, many of which may add to or further the antigencity in some synergistic way. Standard deactivation methods such as high temperature and utilization of formaldehyde which cause denaturation of protein are not used.

In general, the term pathogenic virus denotes any viral agent causing disease in the host. This includes Hepatitus, Influenza, Herpes types I and II, AIDS, Adenovirus, meningitis-causing pathogens and, pneumonia-producing pathogens, etc.

As used herein the Lyme Disease infectious agent to which a vaccine is claimed herein is *Borrelia burgdorferi*.

It has been found that the product of the present invention resulting from appropriate ultrasound treatment, as will be described, of substantially viable viruses, bacteria or cells can be used directly as a vaccine without the necessity for any other physical or chemical treatment. The sonication method described herein does not require any prior preparation of the viruses, bacteria or cells other than obtaining the viruses, bacteria or cells in sufficient quantity by various means. Moreover, besides simplifying the procedure, the elimination of such other treatment reduces the risk of modifying the antigens in such a manner as to diminish their effectiveness in evoking an immune or therapeutic response.

For purposes of this invention, the term vaccine is used herein to describe a product which evokes an immunogenic and/or therapeutic response. Vaccines according to the instant invention may be comprised only of whole cell, bacteria or virus sonicates or may be combined with effective amounts of immunogenic boosting agents, for example, adjuvants or agents to facilitate the preparation or delivery of immunogenic material. Still other vaccines according to the present invention may comprise a supernatant formed from the low speed centrifugation of sonicated whole cells to remove certain, usually large, non-immunogenic cellular particles, either alone or in combination with an effective amount of an adjuvant.

The procedure disclosed herein is far simpler than most if not all of the prior methods used for preparing prospective vaccines including those described in U.S. Pat. No. 3,558,066. These procedures include high speed centrifugation, molecular sieve chromatography of the extracts and supernatants, ion exchange and affinity, chromatography, freezing and thawing, high speed blade homogenization, filtering, mincing, drying, isoelectric focusing, exposure to radiation, formaldehyde, high temperature and solvent extraction, obligate inclusion of adjuvants and the like. Such diverse and complicated methods have previously been employed in various combinations to deactivate, separate, solubilize and purify with the intent of increasing the potency of the antigen but are without the efficacious results of the present invention.

Thus according to the present invention, an entirely new method of obtaining an antigenically active preparation from whole viruses, bacteria or cells is provided which results in a new vaccine.

The present invention also comprises a treatment of substantially viable cells or viruses in such a way as to make available antigens capable of inducing an immunogenic and/or therapeutic response to disease. In particular, this invention relates to a vaccine for producing an anti-*Borrelia burgdorferi* immunogenic response in humans comprising treating whole spirochetal bacteria of *Borrelia burgdorferi*, with sound waves at a frequency and intensity sufficient to disintegrate all of the cells and prepare or reorient the antigens originally present on or with the cell for use as a vaccine without further purification. The spirochetal bacteria sonicates may be used directly or subjected to centrifugation, preferably low speed centrifugation (at less than 1,000× g) to produce an antigen rich supernatant. Both of these immunogenic products may be used directly in vaccines or combined with effective amounts of adjuvant. Thus, the vaccine may comprise an effective amount of the antigen rich whole spirochetal bacteria sonicate alone or in combination with an effective amount of adjuvant.

In still other aspects of the instant invention related to a Lyme Disease vaccine, the vaccine may comprise a whole spirochetal bacteria sonicate utilizing different serotypes (or serovar) of *Borrelia burgdorferi*. The terms "serotype" or "serovar" are used to describe subdivision of a species or subspecies distinguishable from other strains therein on the basis of antigenic character. It is unexpected that the use of whole bacteria sonicate from different serovar of *Borrelia burgdorferi* would produce immunity to the different serovar. Thus, in certain aspects according to the present invention, an important feature is the use of a mixture of effective amounts of bacterial sonicates derived from more than one serovar of *Borrelia burgdorferi* for instilling broad spectrum immunogenicity against *Borrelia burgdorferi* strains and sub-species.

In certain aspects, this invention comprises the treatment of microorganisms or viruses in a liquid with sound waves at a frequency and intensity sufficient to disintegrate all of the cells or viruses. The ultrasonic process both deactivates the potentially harmful cells, bacteria or viruses and prepares or disperses the antigens originally present on or with the cell, bacteria or virus for use as a vaccine without further processing. While not being limited by way of theory, it is believed that the ultrasonic method employed effectively deactivates (disintegrates) all of the pathogenic living cells, bacteria or viruses, and more favorably orients or presents antigens on the surface of the cells or viruses in vesicles which are produced during sonication of the whole cells or viruses.

It is particularly important for the production of a sole and efficacious vaccine that the processing intensity of the ultrasound is sufficiently high enough so that no recognizable morphological entity remains in the homogenate. Particulate matter generally must be in the submicron range to ensure that dispersion and release of antigens is optimal and that no viable organisms remain that might otherwise cause disease.

The method of producing the vaccine through use of ultrasound according to the present invention is conveniently carried out in a liquid medium, and preferably in an aqueous medium.

The material so produced is a vaccine which may be administered to a patient to result in acquisition of immunity or to evoke a therapeutic response to the disease in question.

DETAILED DESCRIPTION OF THE INVENTION

The present invention relates to the process for the preparation from substantially viable cells, bacteria or viruses of a product capable of inducing a protective response when administered to a patient. The present invention also relates to vaccines or other immunogenic dosage forms produced by this method.

The term "viruses, bacteria or cells" used herein refers to any cells, bacteria or viruses with the potential to cause disease in the host. In certain cases for purposes of brevity, the term "cells" or "cell" is used to refer to viruses, bacteria and cells.

The term "spirochetal bacteria of Borellia" refers to the whole bacteria of the genus Borrelia which are responsible for the symptoms associated with Lyme Disease and Relapsing Fever. In the Lyme Disease vaccine aspect of the present invention, the spirochete of *Borrelia burgdorferi* are sonicated and then used directly or in combination with an adjuvant as a Lyme Disease vaccine.

In general, the product of this invention is prepared by first obtaining the viruses, bacteria or cells in question, for example, as by growth in the laboratory in culture medium by fermentation or in suitable host cells. In the case of *Borrelia burgdorferi*, the spirochete can be cultured in vitro under stringent conditions which include reduced oxygen tension and a highly enriched nutrient medium (for example, BSK media). Spirochetes are generally stored frozen (−80° C.) in 30% glycerol or other cryopreservation media and then thawed and used for production. Aliquots of the bacteria are inoculated into 8 ml cultures of BSK media and become confluent (as measured by media discoloration and visible collection of spirochete cells on the tube bottom) in about 7–10 days. The density of the culture at confluence is about $1-3 \times 10^8$ spirochetes/ml. Quantitation of spirochetes are achieved by darkfield microscopy or any other suitable means. Cultures of spirochete are generally harvested by centrifugation (at at least 10,000×g for 15 minutes). The spirochetes are first washed (generally by resuspension in a large volume of PBS and then collected by centrifugation for about 20 minutes at 15,000×g), then suspended in a liquid such as PBS before sonication.

The viruses, bacteria or cells for use in this invention are "substantially viable". The term "substantially viable" means that the cells, bacteria or viruses in question are substantially intact and are capable of continuing to function at the time of sonication. Whether or not a bacteria, cell, bacteria or virus is viable can be determined by known procedures. One such method is the viable cell count in which a dye, Trypan blue, is used to stain a cell sample. The viable cells will not absorb the dye, while a cell that has a loss of viability will absorb the dye. Viable viruses retain the capacity to infect appropriate host cells and can be quantitatively assayed by a number of standard methods (e.g. plaque formation assay). In the case of bacteria, one method of determining substantial viability is to use an amount of the sonicated preparations to inoculate a culture of fresh BSK media. Following effective sonication, no bacterial growth is detected. In addition, administration of sonicated preparations of Bb mice does not cause infection of the mice.

The fact that substantially viable cells, bacteria or viruses are subjected to ultrasound treatment in the procedure of this invention is important because previous loss of viability by means other than ultrasound such as high temperature, chemical disinfectant, radiation, or lack of nutrition tends to result in denaturation of cell components and thus, diminution or degradation of the antigens including the antigens which are intended to produce the host immune response. Degradation of these antigens probably limits their ability to produce a specific immune response and may diminish the immunogenic activity of the vaccine.

After isolation, the substantially viable viruses, bacteria or cells are then subjected to ultrasound treatment, in other words, sound waves in a liquid at a frequency and intensity and for such duration as to rupture essentially all of the viruses, bacteria or cells, without at the same time raising the temperature of the bacteria, cells or viruses and liquid sufficiently to denature key components, in particular antigens.

Treatment in the liquid medium with sound waves at an appropriate frequency and of sufficiently high power level produces cavitation, whereby the structure of the cells, bacteria or viruses in the liquid is disrupted and dispersed.

The term "cavitation" defines a physical process whereby tiny bubbles present in the liquid are made to grow and collapse with great force. This occurrence produces violent pressure changes in the sonicated liquid at multiple microscopically spaced volume elements within the liquid. These pressure changes, which may be thousands of atmospheres in magnitude, break up any clusters of cells or viruses as well as disintegrate the cells themselves, if the cavitation is sufficiently intense, and shear their genetic material, deoxyribonucleic acid (DNA), or ribonucleic acid (RNA). The destructive force of the cavitation depends upon the surface tension of the sonicated liquid and the vapor pressure as well as the magnitude of the change in bubble size, which in turn depends upon the sound intensity and wave length. Other important considerations include the effect of dissolved gases in the liquid and the control of temperature during the entire procedure.

In general, the frequency, intensity and duration of the sonication is such as to disintegrate all of the viruses, bacteria or cells without raising the temperature of the liquid so as to denature the antigenic components. In addition, the DNA or RNA of the viruses, bacteria or cells which encodes their genetic information is sheared to small fragments and is no longer capable of directing cellular replication. The completeness of the disruption of the cells can be determined by known methods including the use of microscopic examination and attempted growth of cells, bacteria or virus from the sonicated preparation.

As a general rule, the sonic waves are introduced into the liquid medium at a frequency of about 20 to about 40 KHZ. Above this frequency range, cavitation intensity is reduced considerably, even at high power inputs, so that the cells, bacteria or viruses may not be fully disintegrated. Below this frequency range, noise from the ultrasonic apparatus becomes objectionable, and the processing equipment becomes large enough to be unwieldy. The minimum intensity (power) of the sonic waves should be about 1 watt/sq cm. when utilizing a 20 KHZ frequency. At this minimum level of power, cavitation is initiated. Preferably, the intensity level at about 20 KHZ is 50 to 175 watts/sq cm. depending on the physical characteristics of the cells, bacteria or viruses. The destructive power of the sonic waves will vary as a function of the frequency of the sonic waves used, with a lower effect being produced at higher frequencies.

In the case of a Lyme Disease vaccine, the cavitation intensity and frequency is preferably 20 kHz ranging from about 20 to about 150 watts/sq.cm, most preferably about 60–100 watts/sq.cm. For producing a Lyme Disease vaccine, it has been found advantageous in the present invention to pulse samples for about 15 seconds at about setting 4–5 (about 25% of output of sonicator, available from Rx Technologies, Inc., Garden City, New York, U.S.A.) and then rested for about 60 seconds in an ice bath. The sample is further sonicated for an additional 3 pulses (about 15 seconds). In general, the duration of sonication may range from about 10 seconds to several minutes or longer and most preferably is performed in at least two installments for about 15 seconds or longer. It is, of course, important to provide a sonication duration and intensity schedule which results in maximum release or exposure of antigens, yet removes any viable bacterial spirochetes from the sonicate.

Other factors which affect the efficacy of the sonication include: temperature; static pressure; concentration of viruses, bacteria or cells in the liquid suspension; the type of liquid employed; the amount and types of viruses, bacteria or cells to be disintegrated; and duration of sonication as well as the amount and type of dissolved gases introduced into the liquid to achieve specific advantages during sonication.

If the material is not properly and completely sonicated, antigen release will not be maximized, and moreover, the processed material when administered, e.g., by injection, may remain somewhat infectious.

As the temperature rises in the sonicated solution, disruption intensity goes down because of increased vapor pressure within the cavitation bubble which in turn cushions bubble collapse. Above 5° C., the vapor pressure rises logarithmically and as the walls of the bubble collapse they are impeded by the increased number of vapor molecules which are now more active as well. Also a rise in temperature may denature the protein antigens. If the liquid medium has a high vapor pressure or low surface tension, or is viscous, there will also be a reduction of bubble collapse intensity.

The sonication is preferably conducted at room pressure and the sample is maintained at a temperature of roughly about zero to 5° C. to avoid not only the build-up of heat which may denature the antigens but also to minimize the activity of cellular enzymes, some of which may degrade the antigens in question.

The duration of time the cells, bacteria or viruses are sonicated will depend upon the nature of the cell, bacteria or virus and the difficulty of disrupting the particular cell, bacteria or virus. The time must be sufficient however to disrupt the viruses, bacteria or cells so that no recognizable virulent cell structure remains. For optimum results, most sub-cellular contents should be solubilized or at least finely suspended in the sub-micron range. For example, a gram of cultured cells may generally require about 3 minutes of sonication.

In the Lyme Disease vaccine aspect according to the present invention, the immunogenic material is prepared by sonication. For sonication of *Borrelia burgdorferi*, samples are placed into a stainless steel chamber in a physiologic buffer (PBS) and chilled on ice. Because of its infectious nature, the sample, in a sealed chamber, is generally attached to the sonicator horn (usually by thread means or some other method) and sonicated for a period sufficient to render the spirochete inactive without substantially affecting the ability of the antigenic proteins to induce an immunogenic response. In the case of producing a Lyme Disease vaccine, it has been found advantageous in the present invention to pulse samples for about 15 seconds at about setting 4–5 (about 25% of output of sonicator, available from Rx Technologies, Inc., Garden City, N.Y., U.S.A.) and then rested for about 60 seconds in an ice bucket or bath. The sample is further sonicated for an additional 3 pulses (about 15 seconds). The duration of sonication may range from about 15 seconds to about 120 seconds or longer in one or more installments.

If the liquid medium contains too much air, cavitation intensity will decrease since the collapsing bubbles will be cushioned by the air molecules within. The processing time may need to be increased in such a case. Antigenicity may be enhanced by dissolving certain gaseous elements and compounds in the solution during sonication. Gases such as hydrogen and helium, because of their low molecular weight, minimize the formation of free radicals that form within the cavitation bubble and cause denaturing. The smaller gas molecules obviate the instantaneous high temperature within the collapsing bubble by quickly transferring heat to the outside of the collapsing bubble surface. Carbon dioxide, cysteamine and sodium carbonate also prevent free radicals from forming and are preferred additives. Carbon dioxide is a particularly preferred additive to minimize the formation of free radicals. Free radicals can easily oxidize or reduce and render sensitive molecules and enzymes useless to the antigenic process.

If the cells themselves are difficult to disrupt such as spores, a higher static pressure in the processing vessel will produce faster results. Cavitation intensity can be increased considerably with the addition of one to two extra atmospheres of gas pressure (15 to 30 pounds/sq. in. or more) over room pressure. It is believed that this phenomenon occurs because air within tiny bubbles, which naturally occur in any solution, is forced out of the bubble volume and dissolves into the liquid. An increase in static pressure may be an advantage if disruption time is to be kept to a minimum. This may be necessary for the purpose of maximizing antigen release or preserving antigen activity.

After sonication of the cells, bacteria or viruses the resulting product is directly available for use as a vaccine. No further additions or purification of the resulting material is necessary. The sonicated vaccine can be injected as is, or for convenience of administration can be added to a pharmaceutically acceptable carrier or adjuvant. Suitable pharmaceutically acceptable carriers will be apparent to those skilled in the art, and include water and other polar substances, including lower molecular weight alkanols, polyalkanols such as ethylene glycol, polyethylene glycol (PEG), and propylene glycol as well as non-polar carriers.

In the case of a Lyme Disease vaccine, sonicated spirochetal bacteria of *Borrelia burgdorferi* may be used directly, or alternatively, centrifuged at low speed after sonication. The resultant sonicated bacteria or supernatant may be used alone or preferably combined with an effective amount of an adjuvant to produce anti-Lyme Disease vaccines according to the present invention.

Dosages of immunogenic material associated with adjuvants and/or carriers will often be about that of the immunogenic material (disrupted cells, bacteria or viruses) alone. Of course, for use as human vaccines, dosages will be set by the prescribing physician considering relevant factors including the age, weight and condition of the patient and the pharmacokinetics of the agent and release characteristics of the agent from pharmaceutical dosage forms of the present invention.

In the Lyme Disease vaccine aspect of the present invention, the dose of immunogenic material depends upon the form in which it is administered. For example, the vaccine will generally contain an amount of protein obtained from bacterial *Borrelia burgdorferi* (one or more serovar) ranging from about 25 micrograms to about 5 milligrams based upon proteins found in the whole bacteria sonicate or in the supernatant fraction after sonication of whole bacteria followed by low speed centrifugation. Thus, the amount of protein used will fall within this range; however, the amount of whole bacterial sonicate or supernatant fraction used in any vaccine form will depend upon the strength of the immunogenic response elicited. The protein administered as vaccine is derived from the total protein content of the spirochete. The amount of protein contained in any sample of whole bacterial *Borrelia burgdorferi* sonicate is generally assayed by the methods of Bradford, *Anal. Biochem.*, 72,248 (1976) or Lowry, *J. Biol. Chem.*, 193, 265 (1951).

The amount of adjuvant used in the Lyme Disease vaccine aspect according to the present invention also ranges from about 25 microgams to about 5 milligram (and preferably about 50 micrograms to about 1 milligram), depending upon the strength of the adjuvant. In general, this range falls within the same range as the amount of protein used. Adjuvant is preferably used in an amount ranging from about $\frac{1}{10}$ to about 10 times the amount of protein used. In the present invention it has been found that RAS adjuvant and *C. parvum* (P) adjuvant are the most effective in enhancing the immunogenic response of the Lyme Disease vaccine. However, other adjuvants may be used effectively as well.

In certain vaccine dosage forms, standard pharmaceutical carriers as described above may be included. The ratio of immunogenic material and in certain cases, adjuvant to carrier will naturally depend on the chemical nature, solubility, and stability of the immunogenic material, as well as the dosage contemplated. For parenteral administration or injection via such parenteral routes as intraperitoneal, intramuscular, subcutaneous, intramammary or other route, sterile solutions of the whole cell sonicates or supernatant resulting from low speed centrifugation are prepared. Preferably, the vaccines according to the present invention and in particular, the Lyme Disease vaccine, is administered via a subcutaneous route.

The vaccines are prepared by exposing whole cells, bacteria or viruses to sonication. The ultrasound treatment can be carried out under either aerobic or anaerobic conditions. Anaerobic conditions can be produced by carrying out the ultrasound treatment in an inert atmosphere such as nitrogen or preferably, carbon dioxide. Sonication under anaerobic conditions may minimize oxidative degradation of the released components. In the Lyme Disease vaccine it has been found advantageous to expose the spirochetal bacteria of *Borrelia burgdorferi* to concentrations of $CO_2$ during sonication.

Under either aerobic or anaerobic conditions, the tremendous disintegrating force of the cavitation process tends to produce the formation of undesirable free radicals. The free radicals may, in some cases, reduce or destroy the efficacy of the antigens. To minimize or eliminate the formation of the undesirable free radicals, suitable gaseous elements or compounds may be dissolved in the liquid suspension during sonication. Gases such as carbon dioxide, hydrogen or helium, among others, can be used. Sodium carbonate and cysteamine are also useful for this purpose. The most efficacious gas appears to be carbon dioxide. With the additional protection from free radical damage when needed, the resultant sonicate preparation, in theory, should have all of the immunogenic properties of a live, unprocessed cell vaccine, perhaps more. In fact, it is presently believed that the sonically treated material may be superior to live cell preparations due to the disruption of cell surface structures and the consequent exposure of formerly cryptic antigens.

The vaccine is preferably administered by a parenteral route of administration or any other suitable route. For parenteral administration or injection via such parenteral routes as intraperitoneal, intramuscular, subcutaneous, intramammary or other route, sterile solutions of the whole cell sonicates or supernatant resulting from low speed centrifugation are preferably prepared. Preferably, the vaccines according to the present invention and in particular, the Lyme Disease vaccine, is administered via a subcutaneous route. The dosage of the vaccine employed and the treatment schedule would follow practices normally employed for other vaccination or therapeutic regimens wherein this general method of treatment is employed (i.e., not as for oral vaccines but as for those typically used to desensitize an individual against allergens or to protect or treat against viral diseases) where more than one inoculation may be required.

Preferably, the dosage schedule for immunization against Lyme Disease in humans or other mammals involves subcutaneous injection of at least about 25 micrograms of protein, most preferably in combination with an adjuvant (in many instances about the same amount of adjuvant as protein, but in certain instances, between $1/10$ and 10 times the amount of adjuvant as protein-amounts outside of these ranges may also be useful). In the case of Freund's adjuvant, the sonicate is emulsified with adjuvant prior to injection. Other adjuvants, preferably RAS and *C. parvum* (P) preferably are used in the manner described by the manufacturer adapted for use in combination with the sonicate of the present invention.

As a general rule, the term "effective amount" refers to an amount effective to produce a protective immune or therapeutic response with respect to a disease for which a vaccine is created. In the case of adjuvant, the term "effective amount" is used as is described hereinabove. An effective amount can be determined by varying the dosage of the product and measuring the resulting cellular and humoral immune and/or therapeutic responses. In general terms for the vaccine, this amount represents approximately about 5 micrograms to about 100 milligrams by weight protein or more (determined by assay, as described herein). In the Lyme Disease vaccine aspect of the instant invention, the effective amount of total protein generally represents about 25 micrograms to about 5 or more milligrams by weight, preferably about 50 micrograms to about one milligram within this range.

The method of the present invention is particularly useful for the preparation of a vaccine for viral diseases. These would include, but would not be limited to, AIDS, Hepatitis, Herpes, Adenovirus and meningitis infections.

In the therapeutic method according to the present invention, a human patient is first inoculated with an effective amount of an immunogenic material in the form of a whole cell, bacteria or virus sonicate (or from the supernatant isolated from a low speed centrifugation of the whole cell, bacteria or virus sonicate) and then the inoculated patient receives a boost of immunogenic material and in certain cases, adjuvant at least once, usually at the time of first inoculation or, in certain cases, at least about three or four weeks after the initial inoculation. In certain instances, an additional boost of immunogenic material and in certain cases, adjuvant may be given to promote the immunogenic response. Additional doses of vaccine may be provided to boost the initial innoculation at about three-four weeks and at about six-eight weeks, respectively.

The following examples are provided for purposes of illustration only and are not to be viewed as a limitation of the scope of the invention.

EXAMPLES

Growth of *Borrelia burgdorferi*-Preparation of Antigen-ELISA Assay

Growth of *Borrelia burgdorferi* spirochetes (obtained from American Type Cell Culture # 35210 ATCC or Alan Barbour, University of Texas, San Antonio, Tex., U.S.A.) in vitro is achieved in BSK media. Bacteria are stored in 30% glycerol at −80° C. Aliquotes are inoculated into 8 ml cultures of BSK media and become confluent (as evidenced by discoloration and visible collection of spirochete on tube bottom) in about 7–10 days. Quantitation of spirochete in nutrient media is achieved by darkfield microscopy using a Petroff-Hauser counting chamber. To prepare vaccines, one or more of the spirochete populations (including different serovar) may be used.

Preparation of antigen by sonication is achieved by harvesting cultures of spirochete (centrifugation at a minimum of 10,000×g for 15 minutes), washing once with sterile cold phosphate buffer solution (PBS), and resuspending the cultures in 20 ml of PBS. The atmosphere is saturated with carbon dioxide by dropping a small piece of dry ice into the sample (the sample may require pH adjustment because of the formation of carbonic acid). Samples are chilled on ice and placed into a sealed stainless steel sonication chamber (available from RxTechnologies, Inc.). The sonication chamber is placed in a bucket of chilled ice water to maintain low temperature.

Enzyme Linked ImmunoSorbant Assay (ELISA)

In brief, the ELISA method used in the present invention uses as antigen the intact spirochete or the derived sonicate. If whole spirochete are used the assay plates are pre-coated with poly-Lysine (1 mg/ml for at least 1 hour) in order to adhere the antigen. Alternatively, the assay plates may be prepared by adhering the sonicated spirochete to the assay plate at 0.01 mg/ml in a volume of about 0.05 ml. The antigen is adhered to the assay plate in a buffer of pH 9.5 $Na_2CO_3$ for at least one hour and then the plate is washed with PBS. Antisera from test animals is applied at various dilutions in PBS (containing 0.1% bovine serum albumin) and allowed to react overnight at 4° C. Plates are thereafter washed with PBS and a second antibody (peroxidase conjugated affinity purified rabbit anti-mouse IgG from Cappel, Inc., Malverne, Pa., U.S.A.) is applied at a dilution of 1:500. The second antibody is reacted for 1 hour and the excess is removed by washing. Bound second antibody is detected by reaction with ABTS (Boehringer Mannheim Co., Indianapolis, U.S.A.) in the presence of $H_2O_2$ for 30 minutes at room temperature. The reaction is stopped by the addition of a detergent and the reaction product is quantified at $A_{405}$ nm using a 96 well plate reader (Biorad, Inc.).

Example 1

Relative Reactivities of Splenocytes Derived From Varying MHC Haplotypes in Proliferation Assays These experiments tested the influence of genetic background (in particular, the influence of MHC Class I haplotype) upon the responsiveness to injection with sonicate derived from *Borrelia burgdorferi*. The assay was the antigen-dependent proliferation assay which measures immune T cell proliferation in vitro. The proliferation assay is a standard immunological assay performed with common reagents. The assay is derived from *Lymphocytes: A Practical Approach*, ed. GGB Klaus, IRL Press, Washington, 1987, Chapter 9.

Spleen cell preparations from mice were prepared as described by Klaus, supra, Chapter 1. The results presented show that all of the various mouse strains tested respond to injection of spirochetal antigens by the production of a splenic T cell immune response (Table 1, below). The Balb/c strain demonstrated a particularly high level of background (non-antigen dependent) and was deemed unsuitable for this assay. The other strains tested were all adequate in terms of responsiveness. It was decided to pursue T cell cloning from C3H and C57bl/6 mice injected with sonicate since these strains of mice develop certain pathophysiologic symptoms of infection that closely mimic the human disease pathology.

TABLE I

| strain | Activity |
|---|---|
| B10 (H2k) | ++ |
| BALB\c (H2d) | +++ |
| C57B1\6 (H2b) | ++ |
| C3H\HeN (H2k) | ++ |
| DBA\2J (H2d) | + |

+++ = Most active splenocytes.
+ = Least active splenocytes.

Example 2

ELISA of Sera of C3H Mice Immunized with *Borrelia burgdorferi* Sonicate $C_3H$ mice were twice immunized with 50 ug of sonicate prepared from whole *Borrelia burgdorferi* spirochete cells (Bb-31) combined with various adjuvants as set forth in FIG. 1. The date of first injection appears in the legend in FIG. 1. The second injection occurred 10 days after the first injection. All adjuvants were obtained from Ribi Immunochemical and were used according to instruction from the manufacturer. In brief, each vial of adjuvant was reconstituted to 2.0 ml in saline and 1/10th (0.2 ml) was taken for mixing with antigen for each injection. Mixtures of antigen and adjuvant were vortexed for 1–2 minutes before injecting by intraperitoneal route.

The individual adjuvants included Ribi Adjuvant System (RAS), *Corynebacterium parvum* (CP) and Bacillus of Calmett and Guerin Cell Wall (BCGCW) are indicated in the legend. The number of injections that were given followed Within parenthesis is shown the number of injections/number of days following the last injection that the assay was performed. The sera was tested by Enzyme Linked ImmunoSorbant Assay (ELISA) assay using total spirochete sonicate as antigen as described hereinabove. The second antibody was anti-IgG.

The results indicated that mice injected twice with sonicate plus adjuvant developed high-titer, long-lived IgG antibodies. Several adjuvants were equally effective in this assay.

Example 3

Proliferation of Spleen Cells Derived from a $C_3H$ Mouse Immunized with Bb-31 *Borrelia burgdorferi* Sonicate A C57bl/6 mouse was injected 2 times with only 0.05 mg of sonicate as prepared above and spleen immune cells were prepared according to the method Klaus, supra, Chapter 1. The effect of different antigens upon in vitro proliferation was tested. As indicated in the legend in FIG. 2, the black bars show data achieved when whole spirochete grown at 33° C. were used as the stimulator in vitro. The cross hatched bars show the proliferation when the spirochete grown at 37° C. were used as stimulator. The effect of different concentrations of sonicate (that used for immunization) was used as stimulator (values are in micrograms per sample well) and the stimulator effect of a single concentration of a non-related bacteria *E. coli* is shown in the stippled graph.

The results, set forth in FIG. 2, indicate that the whole cell sonicate is effectively recognized by T cells in vitro although there is a maximal concentration of effectiveness. There is some recognition of the same strain of spirochete grown at heat shock temperature suggesting that certain antigens are expressed in common between spirochetes grown at physiologic temperature and also at heat shock temperature. *E. coli* does not share crossreactivity with *Borrelia burgdorferi*.

Example 4

Proliferation of Spleen Cells Derived from a C₃H Mouse Immunized with Bb-31 *Borrelia burgdorferi* Sonicate Plus RAS Adjuvant Proliferation assay of splenocytes isolated from a C₃H mouse immunized 2×with 50 ug of sonicate plus RAS adjuvant (amount). The general plan of the proliferation assay is as follows. Spleens are taken at least 10 days after the last injection and mixed with various antigens in the proliferation assay plate. After 5 days of incubation [$^3$H]-thymidine (luCi) is added to the individual wells for 8–16 hours and the radiolabel incorporated into cellular DNA is determined using liquid scintillation counting. Incorporation of thymidine into DNA is a directed measure of DNA replication of the cells (T cells) and that in turn is a measure of the antigen recognition by the T cells under investigation (i.e., a T cell proliferates when stimulated to divide by exposure to its cognate antigen- in this case spirochetes, and not when exposed to either nothing or an irrelevant antigen such as *E. coli*.

Figure 1:
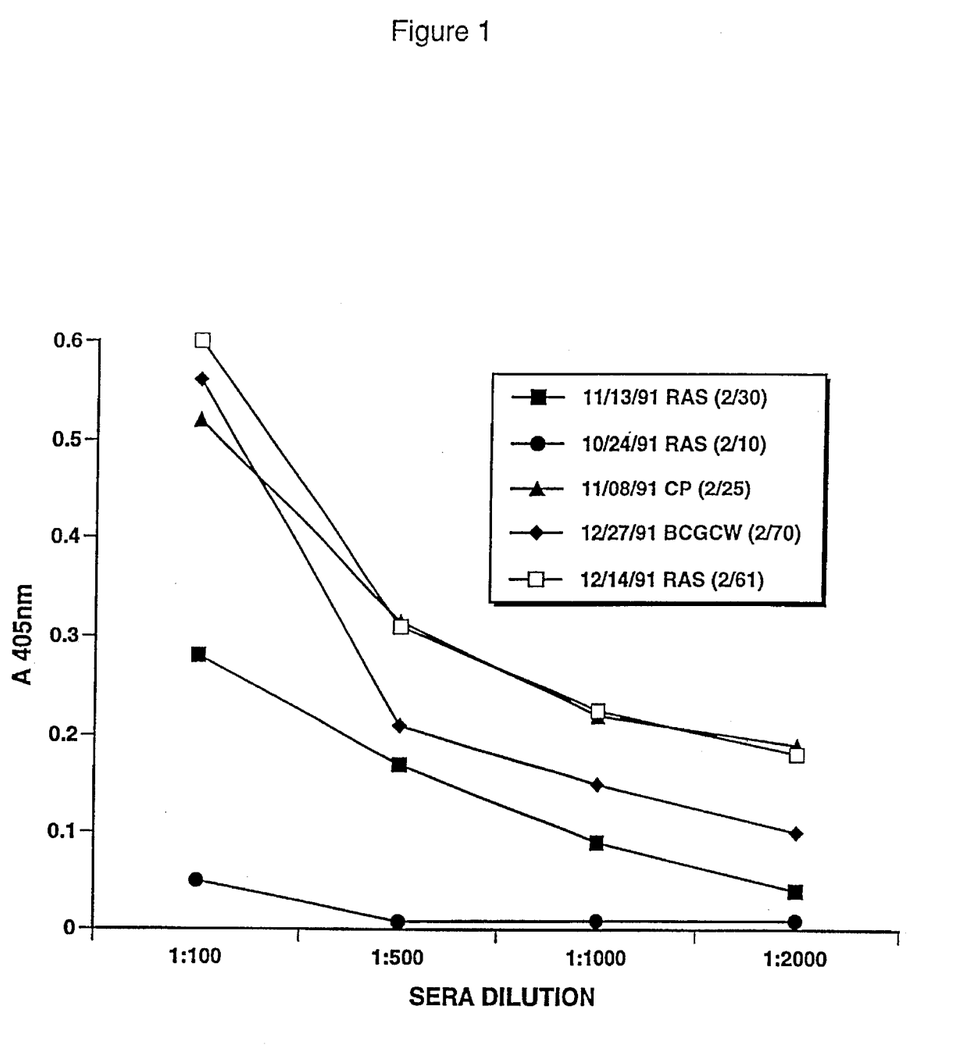
FIGS. 1–7, as described herein, represent graphical data showing the antibody response for mice inoculated with *Borrelia burgdorferi* as set forth in the Examples.
Figure 2:
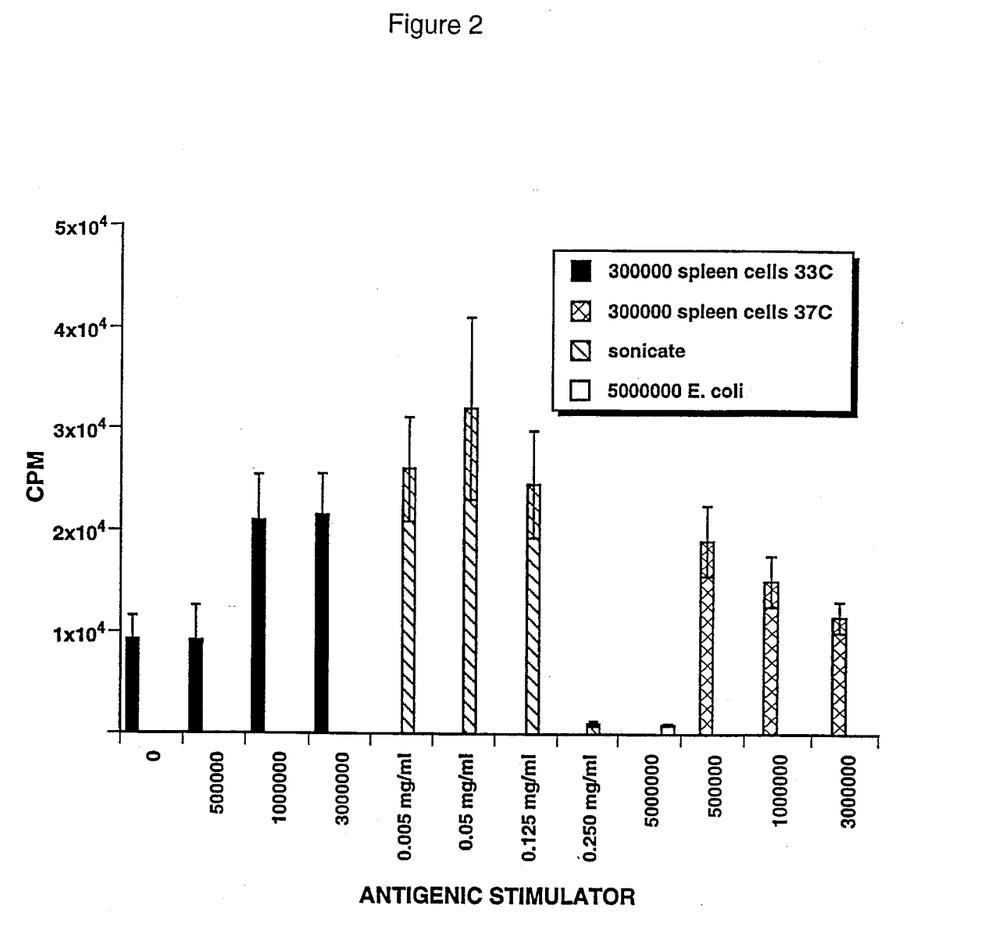
Figure 3:
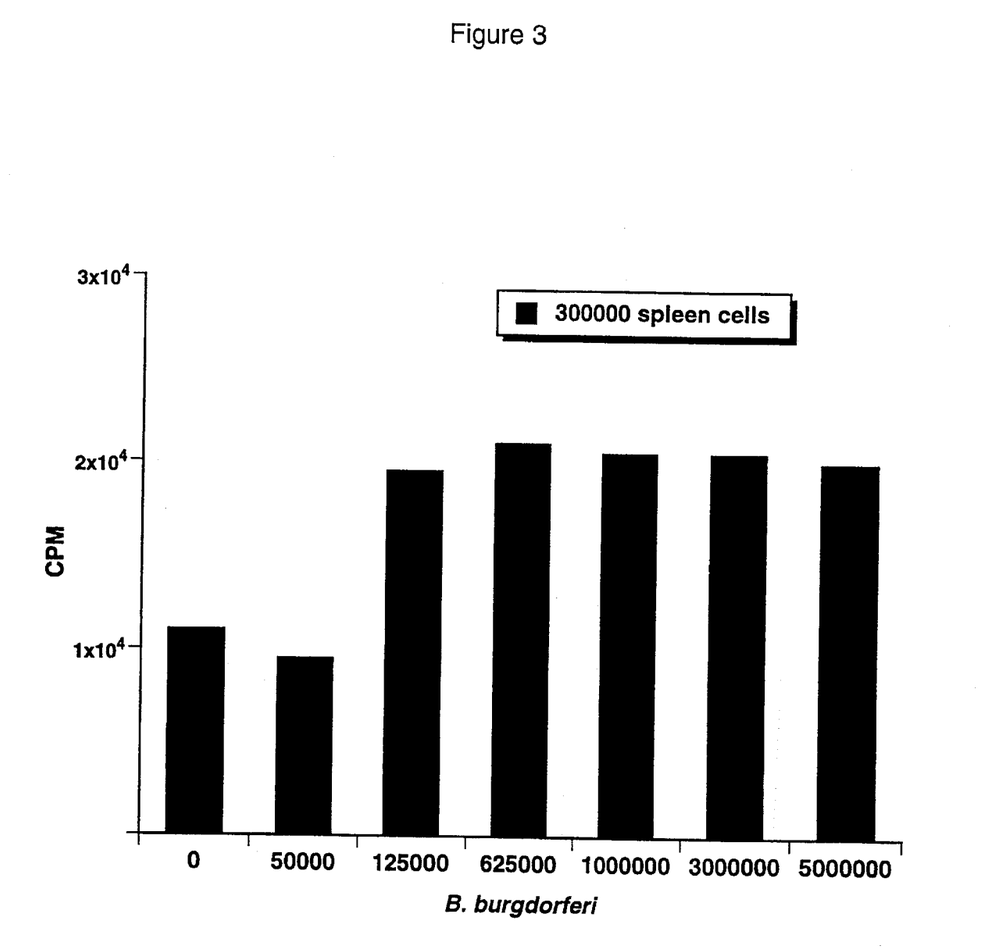

The results, set forth in FIG. 3, indicate that mice injected with *Borrelia burgdorferi* whole cell sonicate as prepared above plus RAS adjuvant developed long-lived spleen-associated, antigen-specific anti-spirochete T cells that can recognize whole spirochete in vitro.

Example 5

Proliferation of Spleen Cells Derived from a C₃H Mouse Immunized with Bb-31 *Borrelia burgdorferi* Sonicate Plus *C. Parvum*

Figure 4:
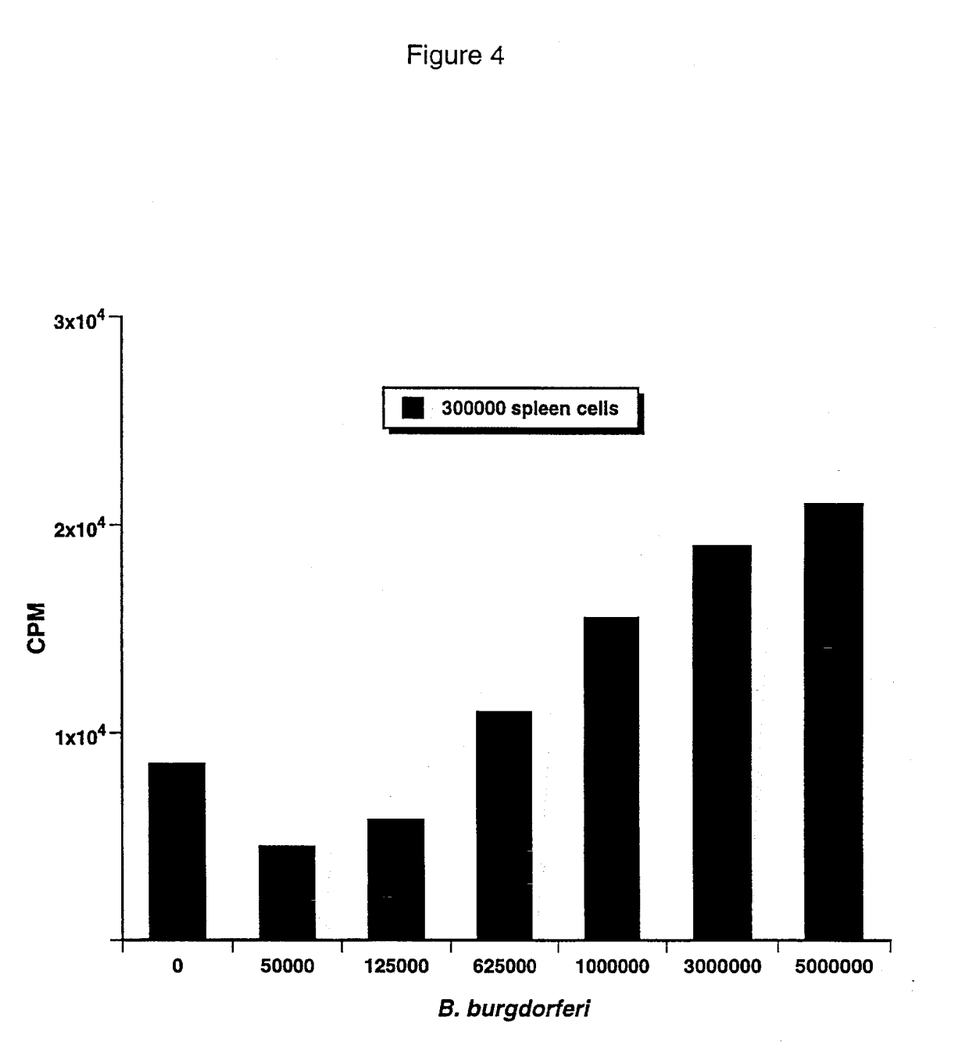

Proliferation assay of splenocytes isolated from a C₃H mouse immunized 2×with 50 ug of sonicate plus 5 ug of *C. parvum* adjuvant. The animals were immunized twice, IP injections about 10 days apart. Proliferation assay performed as described in Example 4, above. The results are set forth in FIG. 4.

The results indicate that mice injected with *Borrelia burgdorferi* whole cell sonicate as prepared above plus *C. parvum* adjuvant developed spleen-associated, antigen-specific anti-spirochete T cells that can recognize whole spirochete in vitro. The mouse presented in FIG. 4 exhibited a high antibody titer, as well, an unexpected result.

Example 6

Proliferation of Spleen Cells Derived from a C₃H Mouse Immunized with Bb-31 *Borrelia burgdorferi* Sonicate Plus BCG(CW)

Figure 5:
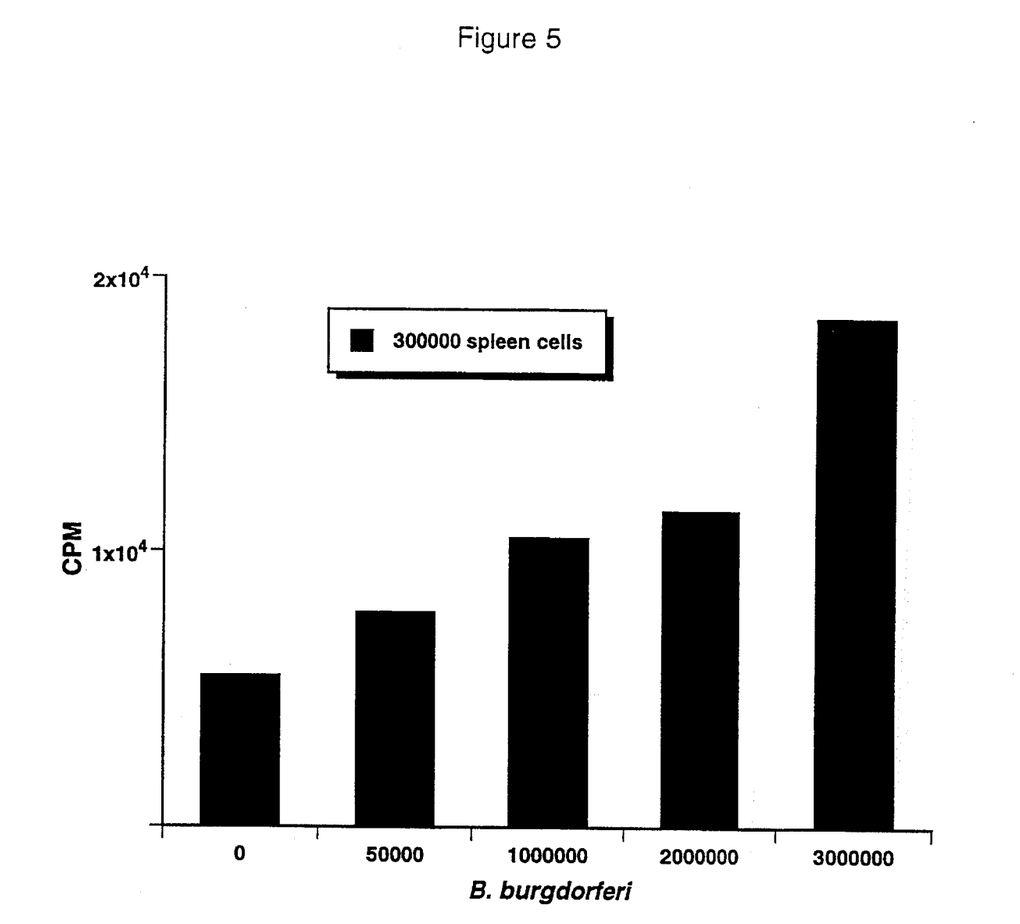

Proliferation assay of splenocytes isolated from a C₃H mouse immunized 2× with 50 ug of sonicate plus 300 ug of BCG (CW) Wall adjuvant per injection (as in Example 4, above). The results are set forth in FIG. 5.

The results indicate that mice injected with sonicate plus BCG Cell Wall adjuvant developed anti-spirochete T cells. The mouse presented in FIG. 5 had a high titer humoral antibody immune response as well, an unexpected result.

Example 7

Presentation of Spirochetal Antigen to Immune T Cells In Vitro Using Immune or Non-immune Antigen Presenting Cells Proliferation assay of splenocytes derived from 2 C₃H mice immunized with 50 ug of spirochete sonicate (protein analyzed) plus 5 ug of *C. parvum*. Each mouse was injected twice at 10 day intervals and were rested for 40 days before isolating and plating splenocytes for two hours on a 15 cm dish to remove antigen presenting cells (APC). APC were isolated by treatment with 1 mM EDTA. The splenocytes were plated at 100,000 cells per well. The APC were given 2300 RAD before using at 1000 cells/well.

Figure 6:
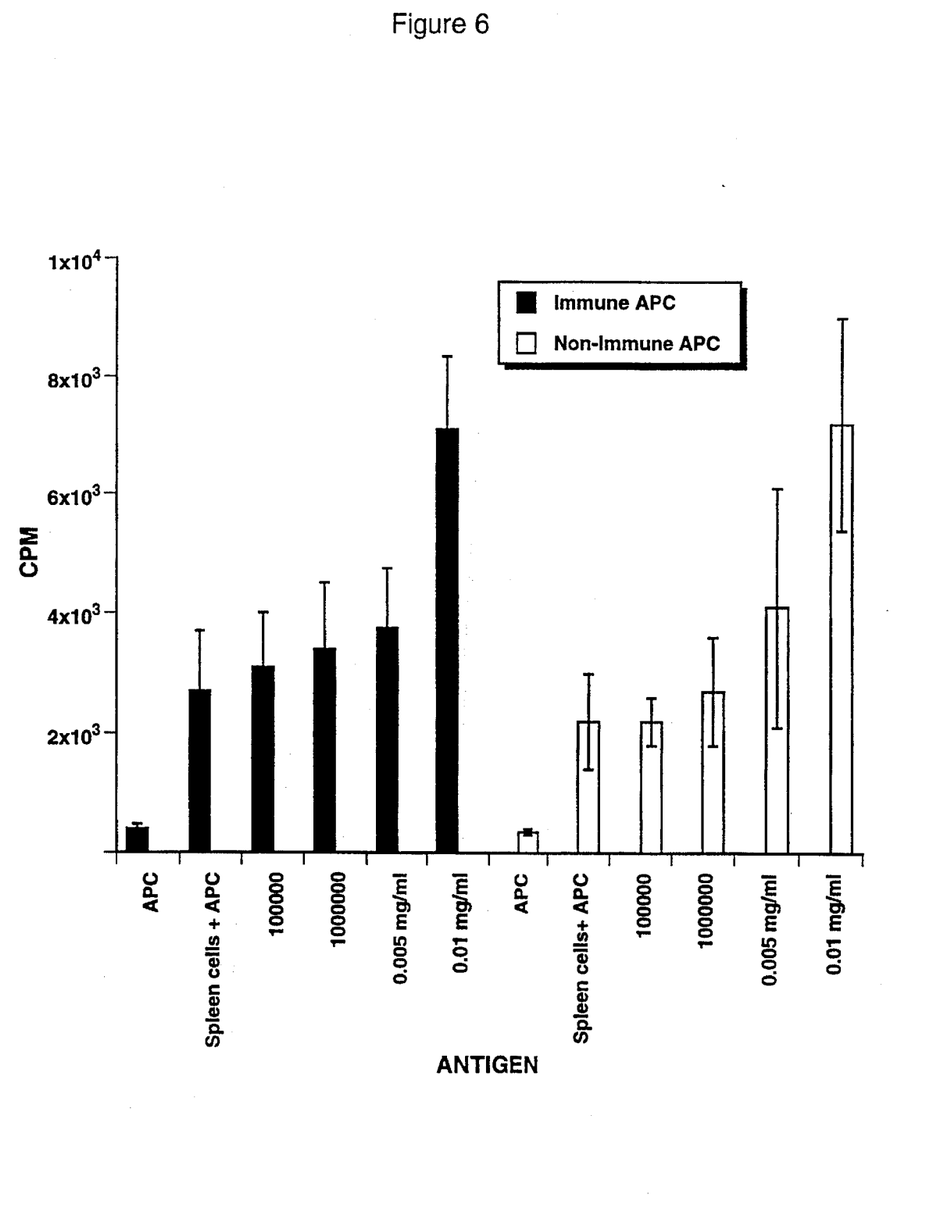

The results as presented in FIG. 6 show that the sonicate of *Borrelia burgdorferi* is effective at stimulating immune T cells in vitro. These results also show that the incorporation of radiolabel into splenocytes is not due to uptake by APC and that non-immune APC can be used to reconstruct in vitro antigen presentation.

Example 8

Long-Term Maintenance of Antigen-Specific Memory T-Cell Immune Response in C57BL/6 Mice Receiving Whole Cell Sonicate of *Borrelia burgdorferi*

C57bL/6 mice received 2 intra peritoneal (IP) immunizations of 50 ug sonicate (no adjuvant except for animal providing data point 'month 3.2' which received sonicate plus 5 ug *C. parvum*) at 10 day intervals. At intervals following the last immunization, spleen-associated immunoreactivity towards either sonicate or whole *Borrelia burgdorferi* spirochete was tested by proliferation assay. The data appears in FIG. 7. The data is plotted as the Stimulation Index for individual proliferation assays which records the maximal stimulation for a given assay divided by the thymidine incorporated into immune splenocytes without antigen.

Figure 7:
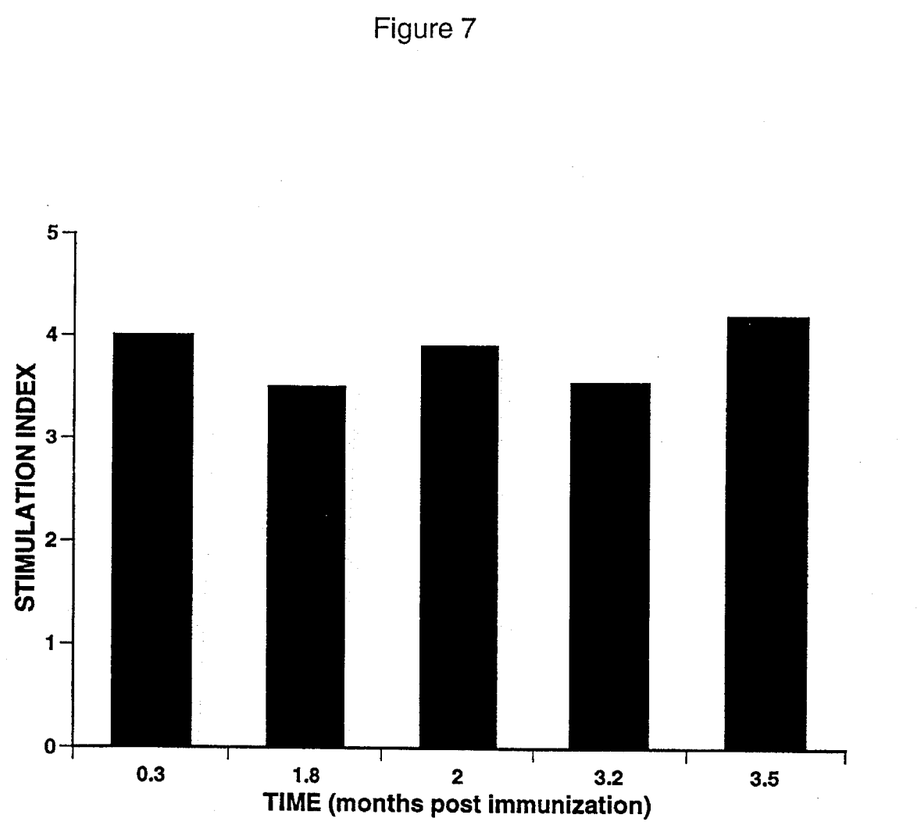

The results indicate that the whole cell sonicate provided long-term immunity in the tested animals. Stimulation index for these animals was as high or higher after 3.5 months as it was 1–2 weeks after immunization.

Example 9

Summary of Immune Response in Mouse Immunizations

The following table 2 summarizes data detailing the immune response of animals achieved by injection with whole spirochete, whole spirochete sonicate or sonicate plus an adjuvant. The first column notes the adjuvant, the second column notes the number of injections an animal received (usually 10 days apart)/the number of days following the last injection that the spleen was harvested for the proliferation assay and sera was obtained for the ELISA assay. The third column (marked "S.I." for stimulation index) shows an index of proliferation which is a reflection of the relative intensity of the immune response and is not complicated by variable background (no antigen) data. The stimulation index is generated from data generated from a thymidine uptake assay wherein the maximal stimulation is divided by the baseline (no antigen control) for each individual mouse.

It is noteworthy that for this group of data, the whole cell sonicate of *Borrelia burgdorferi* exhibited a stimulation index approximately equal to or possibly better than any other sample except sonicate plus BCG(CW) adjuvant, which exhibited the highest stimulation index even 70 days after the last immunization injection.

TABLE 2

| Adjuvant | Schedule | Stimulation Index |
| --- | --- | --- |
| whole spirochete (no sonication) | 2/10 | 2.5 |
| sonicate alone | 2/10 | 3.5 |
| sonicate + RAS | 2/10 | 3.0 |
| sonicate + C. parvum | 2/25 | 2.9 |
| sonicate + RAS | 2/30 | 2.0 |
| sonicate + RAS | 2/61 | 2.4 |
| sonicate + BCGCW | 2/70 | 4.0 |

Example 10

Summary of Antigens and Adjuvants Used in Mouse Immunizations

Adjuvant co-injection with spirochete cell sonicate reproducibly induces long-term, spleen-associated anti-spirochete T cell immune response and also humoral anti-spirochete antibodies. As set forth in table 3 below, the partially purified active component contained in *C. parvum* is particularly effective and easy to use.

The experiments were conducted as follows: Animals were injected with either whole spirochete or else sonicate plus different adjuvants. Animals were injected twice at 10 day intervals and the spleens were used for establishment of the proliferation assay (described hereinabove) 10 days following the last injection. Assignment of relative activity of T cells derived from animals injected with different preparations was made by comparing the absolute levels of radioactivity incorporated into T cells cultured under the identical conditions (same number of T cells together with the same number of spirochetes-$2\times10^5$ T cells plus $1\times10^6$ spirochetes). The results appear in Table 3, below.

TABLE 3

| Antigen | Dosage | Activity |
| --- | --- | --- |
| *Borrelia burgdorferi* Whole Spirochete cell (no sonication) | 1–4 × 10⁷/inj. | +++ |
| *Borrelia burgdorferi* Whole Cell Sonicate | 50ug/inj. | +++ |

| Adjuvant | Dosage | Activity |
| --- | --- | --- |
| BCG Residue | 500ug/inj. | + |
| BCG Cell Wall | 500ug/inj. | ++ |
| C. parvum (P) | 5ug/inj. | +++ |
| C. parvum Residue | 300ug/inj. | + |
| C. parvum Cell Wall | 300ug/inj. | + |
| RAS | 50ug/inj. | +++ |

There are approximately $4.15 \times 10^5$ spirochetes per ug protein in the whole cell sonicate.
Most Activity = +++
Least Activity = +

As evidenced by this example, whole spirochetal bacteria sonicate was effective as each of the sonicates which included adjuvant with the exception of sonicate plus *C. parvum*.

While the invention has been described in its preferred embodiment, it is to be understood that the words which have been used are words of description rather than limitation and that changes may be made within the purview of the appended claims without departing from the true scope and spirit of the invention in its broader aspects.

We claim:

1. A product for administration into a patient as an immunizing or therapeutic constituent comprising a population of substantially viable spirochetal bacteria of at least two serovar of *Borrelia burgdorferi* disrupted by sonic energy without denaturing the protein components thereof in combination with an effective amount of an adjuvant.

2. A vaccine for administration into a patient as an immunizing or therapeutic constituent comprising immunogenic material prepared by disrupting a population of at least two serovar of substantially viable spirochetal bacteria of *Borrelia burgdorferi* with sonic energy without denaturing the protein components thereof, an effective amount of which is combined with a pharmaceutically acceptable carrier.

3. The vaccine of claim 2 wherein said immunogenic material is further subjected to low speed centrifugation to isolate a supernatant which is combined with said carrier.

4. The vaccine of claim 2 prepared under anaerobic conditions.

5. The vaccine of claim 2 prepared by disrupting said spirochetal bacteria in an aqueous medium which minimizes the formation of undesirable free radicals.

6. The vaccine according to claim 2 wherein said immunogenic material is combined with an effective amount of an adjuvant in said carrier.

7. A method for vaccinating a patient against Lyme Disease comprising the step of administering to said patient a vaccine comprising an effective amount of immunogenic material prepared by the sonication of substantially viable spirochetal bacteria of *Borrelia burgdorferi* disrupted by sonic energy without denaturing the protein components thereof.

8. The method according to claim 7 wherein said vaccine is administered as a sterile solution.

9. The method of claim 7 wherein said vaccine contains an effective amount of an adjuvant.

10. The method according to claim 7 wherein said vaccine includes a pharmaceutically acceptable carrier.

11. The method according to claim 9 wherein said immunogenic material is further subjected to low speed centrifugation to isolate a supernatant which is combined with said adjuvant.

12. The method according to claim 7 wherein said immunogenic material is obtained from more than one serovar of *Borrelia burgdorferi*.

13. A method of evoking an immunogenic or therapeutic response in a patient comprising the step of administering to the patient an effective amount of an immunogenic material prepared by disrupting a population of least two serovar of substantially viable spirochetal bacteria of *Borrelia burgdorferi* with sonic energy without denaturing the protein components thereof.

14. The method according to claim 13 wherein said immunogenic material is combined with a pharmaceutically acceptable carrier.

15. The method according to claim 13 wherein said disrupted immunogenic material is thereafter subjected to low speed centrifugation.

16. The method according to claim 13 wherein said immunogenic material is combined with an adjuvant.

* * * * *